United States Patent [19]

Prussin et al.

[11] Patent Number: 4,605,554

[45] Date of Patent: Aug. 12, 1986

[54] ROLL-ON APPLICATION OF AQUEOUS MICROENCAPSULATED PRODUCTS

[75] Inventors: Samuel B. Prussin, Big Sur, Calif.; Ralph Levine, East Hills, N.Y.; Warren J. Hintz, Coltsneck, N.J.

[73] Assignee: AE Development Corporation, Minneapolis, Minn.

[21] Appl. No.: 692,326

[22] Filed: Jan. 17, 1985

Related U.S. Application Data

[63] Continuation of Ser. No. 275,314, Jun. 19, 1981, abandoned.

[51] Int. Cl.$^4$ .......................... A61K 7/32; A61K 7/34; A61K 7/36; A61K 7/38
[52] U.S. Cl. ................................. 424/66; 252/522 R; 424/65; 424/67; 424/68; 424/69
[58] Field of Search ....................... 424/66, 65, 68, 67; 401/220

[56] References Cited

U.S. PATENT DOCUMENTS 2,719,314 10/1955 Taube .................................. 401/220
3,069,718 12/1962 Brady et al. ........................ 401/220
4,110,427 8/1978 Kalat ..................................... 424/66

OTHER PUBLICATIONS

Ash, Formulary of Cosmetic Preparations, 1977, pp. 9 to 15.

*Primary Examiner*—Dale R. Ore
*Attorney, Agent, or Firm*—Marvin E. Jacobs

[57] ABSTRACT

A material (14) such as an antiperspirant contained in a shear-sensitive, free-flowing, powdery, suspension of aqueous droplets stabilized by a barrier of very fine, hydrophobic metal oxide is dispensed from a roll-on applicator. As the ball (18) is rotated, an adherent film (22) of the suspension passes through the annular outlet (20) and is subjected to shear forces. The suspension coalesces into a film (24) of cream or lotion. The suspension exhibits excellent flowability through the outlet (20) without any binding or fouling and the lotion or cream film has good adhesion to the ball. Application results in a dry feeling on the skin of the subject, a short dry-out time and excellent antiperspirant efficacy.

10 Claims, 2 Drawing Figures

ROLL-ON APPLICATION OF AQUEOUS MICROENCAPSULATED PRODUCTS

This is a continuation of application Ser. No. 275,314, filed June 19, 1981, abandoned.

TECHNICAL FIELD

The present invention relates to the dispensing of materials from a container and, more particularly, to a novel roll-on application of a water droplet-in-air suspension and system for dispensing such materials.

BACKGROUND OF THE PRIOR ART

Pressurized dispensing systems, commonly referred to as aerosols, experienced first significant commercialization in the early 1950s resulting in a proliferation of products.

Despite their high costs, aerosol products gained immediate consumer acceptance. The single most important factor behind this success story is the convenience offered by these pressurized products.

Recently, the aerosol market was thrown into a state of disarray as a result of the Rowland-Mollina ozone depletion theory which hypothesizes that a certain percentage of halohydrocarbon propellants find their way to the stratosphere causing a depletion of ozone in that stratum. With a depletion of the ozone in the stratosphere, a greater amount of ultraviolet radiation enters the atmosphere resulting in an increased incidence of skin cancer.

Packaging alternatives of halohydrocarbon propelled aerosols include: products propelled with liquefied hydrocarbon propellants (LPG) such as butane, isobutane and propane and mixtures thereof. Because of the flammability of the LPG gases a substantial amount of water is necessary in the formulation to provide a dousing effect. Products propelled with compressed gas propellants such as nitrogen or the more soluble nitrous oxide and carbon dioxide are usually quite wet because their low solubilities and low concentrations (as compared with halohydrocarbon and hydrocarbon propellants) deprive the product of breakup power. Combinations of liquefied and compressed gas propellants offer no synergistic advantage in terms of achieving a dry spray.

There are, also, the ever-present dangers of aerosols: flammability (in the case of hydrocarbon propelled products), explosion hazard, inhalation toxicity potential, inadvertent misuse of product, valve malfunction, etc.

Pump sprays are high cost, low efficiency substitutes for pressurized products. Antiperspirant pump sprays are currently on the market as non-aerosol counterparts. Their acceptance, has been poor primarily because of the wetness of the application.

Other packaging forms including separative devices, elastomeric membranes with a memory, spring loaded devices, etc., are of little commercial value because of the inordinately high cost, the exotic nature of the hardware and the lack of basic improvement over existing lower cost systems.

In addition to spray application, another means of applying antiperspirant products is by powder application. The major disadvantages of conventional powder products include dusting and lack of adhesion.

In 1979, sales of roll-on antiperspirant and deodorant increased significantly due to the disenchantment of the public with aerosol products and the introduction of new products in roll-on form such as the suspension of antipersipirant salts in a volatile silicone (Gillette's "Dry Idea") and powder roll-ons (such as Carter Product's "Arrid Dry Powder Roll-on"). Roll-on deodorants/antiperspirants are, additionally, more effective than other product forms such as aerosol and pump sprays in reducing sweat.

Roll-on deodorants and antiperspirants, however, suffer from the lack of application aesthetics. The average aqueous roll-on lotion takes a long time to dry and passes through an uncomfortable sticky and tacky stage prior to drying. Attempts to overcome these negative attributes have not been entirely successful. The solution to one problem gave rise to other problems. For example, although the suspension of antiperspirant salts applied by roll-on means eliminated the sticky/tacky sensation, the oiliness from the volatile silicone vehicle persists for fifteen minutes, more or less.

Although dry powder roll-ons eliminate the sticky/-tacky sensation and are not oily, the adhesion of the application is very poor; the powdery material falls out on the clothing and in the general vicinity of the application. The powder does not flow readily between the ball and housing and the net result may be less than the desirable amount of product applied to the axilla with commensurately less efficacy.

Recently, it was discovered that aerated, hydrophobic metal powder oxide microencapsulated aqueous droplets could be formulated in a powder-like dry feeling shear-sensitive suspension. However, when this suspension is subjected to shear such as by passage through the outlet orifice of a spray container or by rubbing, combing, etc., the droplets coalesce to form a smooth, elegant cream or lotion having good adhesion to a surface.

Bioaffecting materials such as antiperspirants or deodorants can be added to the powder or aqueous phase of the bulk liquid-in-air emulsion or suspension without affecting its ability to form a stable, shear-sensitive suspension or its ability to dispense the particles thereof. The microencapsulated suspension is the subject of U.S. patent applications Ser. Nos. 29,630 and 160,673 now issued as U.S. Pat. Nos. 4,278,206 and 4,364,515, respectively.

Roll-on applicators operate by attaching material to the underside of the ball and conveying the suspension to the axilla where it is deposited. It was not known nor believed that the powdery-like suspension would adhere to the ball since it does not adhere to most surfaces nor was it known whether the powder suspension nor the sheared lotion or cream form thereof would permit consistent operation of the roll-on applicator without fouling or seizing of the ball.

BRIEF SUMMARY OF THE INVENTION

It has now been discovered in accordance with this invention that the free flowing, powdery aqueous suspension can be reliably dispensed from a roll-on applicator. The suspension exhibits excellent flowability through the annular space between the ball and socket without any binding or fouling. The suspension when sheared has good adhesion without undesirable powder fallout. The application of an antiperspirant from the aqueous suspension by roll-on results in a dry feeling on the skin of the subject, a short dry-out time, and excellent efficacy equalling or exceeding the sweat reduction of an aqueous solution of the same antiperspirant used as a control for these studies. The product is absent stickiness, tackiness, oiliness and long dry-out time of conventional lotion roll-on applications. The efficacy is substantially higher than the earlier squeeze-bottle spray version and in some tests exceeds the efficacy of aqueous solution of the same antiperspirant compound.

During application of the air emulsion suspension by roll-on, shear is applied to the suspension during passage through the ball-fitment and/or by rubbing between the ball and the axilla. The powdery substance which is an aqueous, aerated microencapsulation of the bioactive, fragrance, cleansing or other agent desired to be conveyed to the substrate can be adjusted to a shear sensitivity for the given application.

A roll-on dispensing system generally includes a container having a compartment for receiving the bulk liquid-in-air suspension and a seat member for receiving a rotating ball defining therebetween an annular outlet for dispensing the composition. The container or ball can be plastic or glass. The annular outlet dimension or clearance of the orifice can be sized to pass the powdery particles with or without shear, generally with shear destabilization as the particles pass through the orifice. The complete or partial destabilization to a continuous or lotion-like dispersion of powder in the water phase can occur after deposit of the suspension on the surface with rubbing.

Whereas, propellant aerosol or pump sprays must have small particle size and must have little or no water or alcohol to deliver a dry application, the system of the present invention can have a large particle size and can contain substantial amounts of water (60–70%) and still dry quickly. It is surprising that the substantial amount of water in the formulation of the invention does not deter the quick dry out of the dispensed material.

It is important to emphasize that the products of the invention are not powders. Although existing in "powdery form" they differ from powders in virtually all respects; a more accurate description for the aqueous encapsulated vehicle component of the system is detailed in Table 1.

applicator and subsequent application to the substrate, the microencapsulated powdery substance is converted to a lotion with good adhesion. The more shear resistant the bulk, the drier the lotion. The shear sensitivity of the bulk is determined by the time and intensity of mixing, the nature and amount of hydrophobic metal oxide, the nature and amount of system affecting additives, the nature and amount of the bioactive substances or other substances such as fragrance, and other factors. The net shear effect, however, is the sum of the shear effects of the product as it passes through the annular space comprising the ball and housing dispenser and applicator, and the subsequent shear effect of the ball applicator applying the product to the substrate.

The system of the invention provides all or any combination of the following properties: good adhesion to target, nonocclusiveness, breathability, good coverage of target area, no build-up, is noncaking in the package and on the skin, has good slip properties, provides controlled cooling, is cosmetically elegant and is a safe, effective and economical product.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
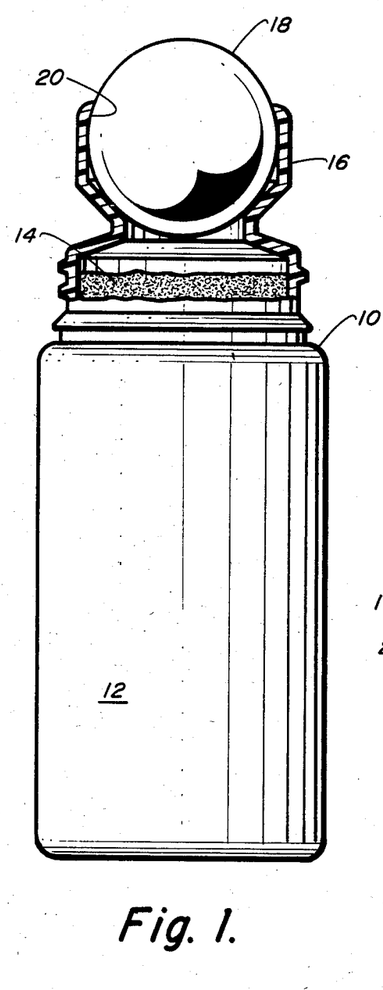
FIG. 1 is an elevational, partially in section view of a first embodiment of a roll-on application system of the invention.

Referring now to FIG. 1, the roll-on dispension system includes a container 10 having chamber 12 receiving a charge 14 of the water-in-air emulsion or suspen-

TABLE 1

| | Powder | Aqueous Encapsulation |
| --- | --- | --- |
| SOLIDS | Principally solids in most cases; incapable of absorbing appreciable fluids and remaining particulate and free flowing. | Can contain up to 90% $H_2O$ and remain particulate and free flowing (actually a water-in-air emulsion). |
| PHYSICAL STATE | Powder | "Powdery substance" with fluid properties. |
| PARTICLE SIZE | Fixed | Capable of being controlled during dispensing and application. |
| DENSITY | Fixed | Capable of a wide range of adjustments; density can be altered during dispensing and application. |
| FORMULATION FLEXIBILITY | Very limited | Extremely broad |
| TOPICAL APPLICATION | Slip and feel of talc at best | Can be dispensed as a dry powder or can be rubbed out as a cream or lotion, depending on product attributes desired. |
| DISPENSING CHARACTERISTICS | As a powder | As an aerosol, as a powder, or as a roll-on. |
| SOLIDS LOAD | Approximately 10% maximum in aerosols before valve malfunctions. | No upper limit in non-pressurized dispensing system. |

Bioactive materials such as astringents or antimicrobial agents, or other materials such as fragrances or pigments used for makeup products can be introduced in either the aqueous or hydrophobic metal oxide phase or in both phases. The shear sensitivity of the bulk is adjusted so that on its passage through the roll-ball sion containing an antiperspirant and/or deodorant. The top of the container contains seat member 16 for receiving a rolling ball 18 defining an annular outlet 20 therebetween.

Figure 2:
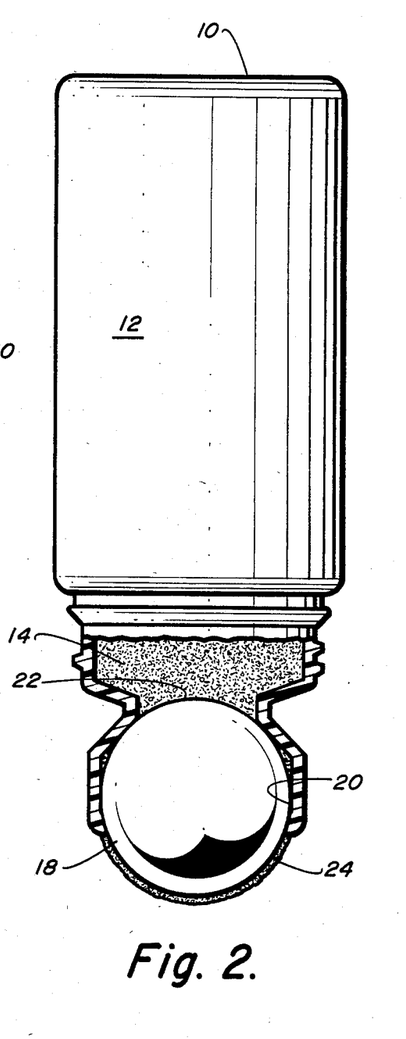
FIG. 2 is an elevational partially in section view of the system of FIG. 1 shown in inverted position.
Figure 3:
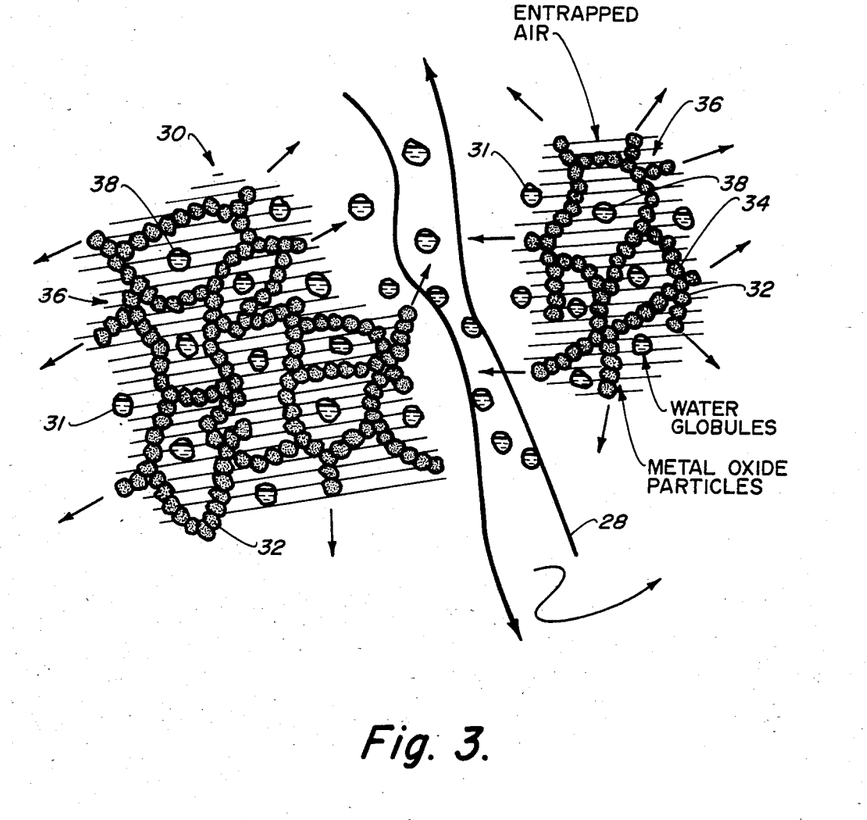
FIG. 3 is a schematic view illustrating the suspension.

Referring now to FIG. 2, the container 10 may be inverted prior to use. The suspension 14 will slide and flow by gravity downward and move into contact with underside of the ball 18 forming an adherent film 22 on the bottom surface of the ball 18. As the ball is rotated and the film 22 passes through the annular outlet 20, the suspension is subjected to shear forces and the suspension coalesces into a continuous or semi-continuous cream or lotion film 24 on the top surface of the ball 18. The powder barrier is disrupted and dispersed into the now continuous water phase. Usually the ball is rolled onto the underarm 5 to 15 times to dispense 40 mg to 400 mg of suspension, usually 75 to 300 mg. The degree of shear imparted depends on the pressure and velocity of the ball and the clearance through the annular outlet. The ball may be smooth or rough and can be formed of glass, metal or synthetic resin such as polystyrene or polypropylene.

It is difficult to specify the optimum clearance since there appears to be wide tolerances of the order of several mils permitted in the available commercial fitments and balls. Furthermore, the more rigid ball is mounted in a more flexible fitment member and can move up and down in the fitment depending on the pressure applied by the user. This, of course, will affect the clearance during application of the suspension. The commercial ball-fitments utilized for antiperspirants do provide pickup, shear and deposition of the suspension of the invention.

FIG. 3 illustrates the microencapsulated aqueous phase 30. In the manufacturing process, the primary hydrophobic metal oxide particles 32 fuse together to form chained particles 34 which have a strong tendency to interact with each other to form a three dimensional network or lattice structure 36 encapsulating discrete water globules 38 with approximately seventy parts of air trapped in the void space. When the aqueous phase and the hydrophobic metal oxide are subjected to high shear mixing the aqueous droplets 38 are trapped in the three dimensional lattice structure, where air is the continuous phase of the dispersion. The air cushioned hydrophobic aggregates surround the small aqueous droplets preventing coalescence and stabilizing the system. When the shear potential is exceeded, such as during travel through the outlet 20, the aqueous phase will coalesce in a whole or in part. Total coalescence can occur on the target surface by rubbing the material on the body.

Optimum functioning of the system and delivery of the desired material depends on the dispensed particle size and its density, the changing size and density of the particles on the ball and on the target, the delivery rate, the degree of hydrophobicity and the nature of the application (dry, moist or creamy). Optimum functioning of the system also depends on the shear stability of the suspension which, in turn, is influenced by the following factors:

1. The ratio of the hydrophobic metal oxide to the aqueous phase;
2. The type of hydrophobic metal oxide used;
3. The amount and nature of the actives;
4. The amount and nature of the system affecting additives;
5. Processing techniques;
6. Delivery system parameters.

Synthesis of hydrophobic metal oxide by reaction of metal oxides and metalloid oxides, particularly colloidal silicas, with various organosilicon compounds has been rather extensively developed. Various organosilicon compounds bearing at least one functional moiety per molecule can be reacted through said functional moiety with the hydroxyl groups existing on the surface of the metal or metalloid oxides. The resulting reaction product is characterized as a metal oxide or metalloid oxide having chemically bonded to the surface thereof organosilicon groups represented generally by the formula:

$$eO—MR_aX_b$$

where e represents the oxide surface; O is oxygen; M is a metal or metalloid such as silicon, each R is any alkyl, aryl, arylalkyl, alkoxy or aryloxy group, a is a number from 1 through 3, X is any halogen or hydroxyl group b, is a number from 0 through 2, and $a+b=3$.

The organosilicon groups are introduced onto the surface of the metallic oxide in an amount sufficient to render the surface of the metal oxide hydrophobic. Generally, at least 50% of the available oxygen groups on the surface such as silanol groups are converted, typically about 70%. Hydrophobic, pyrogenic silica can be produced in accordance with the teachings of U.S. Pat. No. 3,393,155 or other patents such as U.S. Pat. Nos. 2,510,661, 2,589,705, 2,705,206, 2,705,222 and 3,023,181.

In preparing the dispersion of aqueous liquid in fine solid particulates for use in the present invention, in addition to or in place of the hydrophobic pyrogenic silicas used in U.S. Pat. No. 3,393,155 other strongly, hydrophobic metallic oxides having an average equivalent spherical diameter of less than about 100 millimicrons, typically from 1 to 20 millimicrons, can also be used. For example, other finely divided oxides such as aluminas, titanias, zirconias, vanadium oxides, iron oxides or mixed oxides with or without silica can form the basic oxide particles whether produced pyrogenically or otherwise, e.g., by wet precipitation techniques. Also, wet precipitated silicas such as those produced by acidification or neutralization of aqueous alkali metal silicate solutions make ideal starting materials when available in particulate form of the desired fineness. For example, U.S. Pat. Nos. 2,865,777, 2,900,348, 2,913,419, 2,995,422, 3,010,791, 3,034,913, 3,172,726, 3,208,823 and 3,250,594 describe a few of the many different techniques for precipitating particulate silicas from aqueous medium in a form which is sufficiently non-sticky and non-gelatinous to be washed, filtered, dried and subdivided to colloidal powder form.

Specific examples of organosilicon compounds which are often reacted with colloidal metallic oxides to form surface structures like those described above are: organohalosilanes such as $(CH_3)_3SiCl$, $(CH_2)_2SiBr_2$, $(CH_3)_2SiCl_2$ and $(C_4H_9)_3SiCl$; organosilylamines such as $(CH_3O)_3Si(CH_2)_3—NH(CH_2)_2NH_2$ and $(CH_3O)_2(CH_3)SiCH_2CH(CH_3)—CH_2NHCH_2CH_2NH_2$; organodisilazanes such as $(CH_3)_3SiNHSi(CH_3)_3$ and $(C_4H_9)_3—SiNHSi$ $(C_4H_9)_3$, etc. In most cases, the surface treatments must be sufficient to attach organo groups totaling at least 0.5 percent and preferably at least 1 percent by weight based on the dry weight of the metallic oxide particles treated. In many cases, especially with the most preferred high surface area oxides, the concentration of organo groups thereon will equal 2 percent or more by weight.

Examples of commercially available hydrophobic silicas are described in the following table.

TABLE 2

| Silica | Type | Source |
| --- | --- | --- |
| QUSO WR50 | Wet Precipitation Process | Philadelphia Quartz |
| QUSO WR82 | Wet Precipitation Process | Philadelphia Quartz |
| Aerosil R 972 | Fumed Silica-Pyrogenic | Degussa |
| Tullanox 500 | Fumed Silica-Pyrogenic | Tulco Inc. |

The metal oxide starting materials contain substantial amounts of occluded air in a stable configuration. The air is retained in the hydrophobizing reaction resulting in a very low apparent density, i.e., as low as 0.04 g/cc; the real density of the hydrophobic metal oxides is about 2 g/cc. The density of the water-in-air emulsion can be from about 0.30 to 1.5, generally from about 0.45 to 0.90.

The pyrogenically produced metal oxides have more occluded air than do their precipitated counterparts and result in a lower density bulk. For any given system the pyrogenic material contributes considerably more shear resistance to the bulk than do precipitated metal oxides. Thus, if a more shear prone, moist to creamy application is desired, a precipitated metal oxide may be more desirable than the pyrogenic variety; conversely the pyrogenic metal oxide will provide a more shear resistant, drier application. Based on the number of controllable variables, however, each type of metal oxide can be formulated to yield the entire spectrum of application characteristics.

The ratio of hydrophobic metal oxide to aqueous liquid can be from 1/1 to 50/1, generally from 5/1 to 20/1. If the ratio of the hydrophobic metal oxide to water is high (all other factors being equal) the encapsulated aqueous base will be more shear resistant as a result of the mechanical crowding of the hydrophobic metal oxide particle at the aqueous/air interface and additional energy or scrubbing action will be required as the bulk passes through a given annular outlet to effect shear (if such is desired) resulting in the coalescence or partial coalescence of the aqueous phase with an increase in both particle size and density; conversely, if the ratio of hydrophobic metal oxide to the aqueous phase is low, the bulk will be more shear prone as it passes through the annular outlet.

Formulations useful in the present invention normally contain 1–15% by weight of hydrophobic metal oxide, 25 to 98.9% by weight of water and 0.1 to 60% by weight of dispensible material.

Processing is vital to achieving the desired degree of shear resistance for a given roll-on system. The minimum amount of mixing to form the water-in-air dispersion will provide the greatest degree of shear stability when the bulk passes through a given outlet. As mixing continues the bulk will collapse to form a totally coalesced creamy material. Processing is also a function of the type of hydrophobic metal oxide used. Pyrogenic hydrophobic metal oxides will tolerate substantially more shear than identical systems made with precipitated hydrophobic metal oxides. Generally, the preblended solids are added to a vortex of the liquids in a high speed mixer such as a blender and mixed for 2 to 600 seconds, generally 5 to 300 seconds. Alternatively, the preblended powders and aqueous liquid phase are combined and then blended as above.

The shear potential or resistance of the system is an aggregate of the entire shear experienced during passage through the annular outlet resulting in partial or total coalescence of the aqueous phase, the further shearing of the bulk by rubbing on the skin causing additional coalescence.

The elegance and function of the lotions and creams (from the "powdery substance") for cosmetic and pharmaceutical and household applications are enhanced by the incorporation of materials for the purposes indicated. These materials include well tolerated humectant polyols such as glycerin, propylene glycol and sorbitol; sun screening agents such as para-aminobenzoic acid and other benzoate and cinnamate derivatives; deodorant chemicals such as formaldehyde donor compounds and halogenated phenyl and other aromatic derivatives; antiperspirant chemicals such as aluminum and zirconium salts; therapeutic substances including steroids and antibiotics; pigments of the type normally used for make-up items such as for face powders, lipsticks, eyeshadows and rouges; cleansing surfactants of the anionic, nonionic and amphoteric types including ethoxylated phenoxyphenol derivatives, alkyl sulfate salts and imidazolinium derivatives; viscosity modifying agents including polyvinyl pyrolidone, water soluble acrylate and cellulose polymers and natural gums including guar, alginate and carraghenates; and emollient, conditioning and modifying agents including ethoxylated and propoxylated fatty esters, sucrose fatty esters, lanolin derivatives and cationic polymers normally used to condition the hair and skin. Metallic fatty esters such as aluminum, magnesium, calcium and zinc stearates are useful to improve adhesion to the skin. Starches and fine talcs may be incorporated in the system to improve the feel of the product on the skin. Fragrance and color may be added as desired.

Other additives include oils, solvents and surfactants. Generally, chemicals with a high hydrogen bonding capability are better tolerated by the system than intermediate to low hydrogen bonding chemicals. Thus, for solvents, ethanol, glycerol or propylene glycol are better tolerated than xylenol or chlorinated solvents; for surfactants, linear alkyl sulfates are better tolerated than ethoxylated fatty acids although when the ethoxylate is the predominant portion of the molecule (such as FEG 2000 stearate) the surfactant becomes less oleophylic and is better tolerated by the system. Virtually all oils have a profound effect on the system. The mechanism involves the wetting out of the hydrophobic metal oxide resulting in the displacement of air and the collapse of the system. Additives such as lipids, may, however, be introduced into the system by dispersing them in the aqueous phase as an oil-in-water emulsion or by incorporating them into the system as spray-dried powders. Thus, it can be seen that controlled destabilization resulting in the desired degree of shear when the bulk passes through the outlet can be obtained by the judicious addition of relatively non-hydrogen bonding solvents, surfactants and lipids; these materials may contribute to humectancy, creaminess and elegance of application.

The basic system is extremely hydrophobic notwithstanding the fact that it can contain as much as 90% water. The system notwithstanding the water content assumes the properties of the hydrophobic metal oxide. Hydrophobicity is highly desirable in many products, including make-up items and certain topical pharmaceuticals to provide long-term protection while resisting wash-off by the elements and body fluids or to protect the affected area from moisture and provide a protective, controlled release matrix for the actives. The degree of hydrophobicity can be altered by modifying the hydrophobic interface. When the cohesive forces of the hydrophobic barrier are reduced, the bulk becomes more shear sensitive, the degree of coalescence and breakdown of the aqueous phase being a function of the intensity of shear as the bulk passes through the annular outlet plus any subsequent scrubbing action on the skin.

The water sensitivity can also be controlled by controlling the hydrophile-liphophile balance of the system, or by the introduction of hydrophyllic components such as hydrophyllic hydrocolloids or hydrophyllic metal oxides in sufficient quantity to disrupt the hydrophobic metal oxide barrier and provide the desired degree of hydrophyllicity.

A very particular application of the system of the invention is in the dispensing of an antiperspirant. A suitable general formulation follows:

| Ingredient | Amount, % W/W |
|---|---|
| Antiperspirant | 5-45 |
| Hydrophobic silica | 3-10 |
| Metal stearate | 0-5 |
| Water | 30-80 |
| Shear controlling agent, e.g., ethanol or surfactant | 0-5 |

Other additives such as talc or insoluble starch can be added to the formulation in amounts up to 25%, preferably 5 to 15%.

Dispensing of antiperspirant is one of the primary applications of the system of the invention. The U.S. Department of Health, Education and Welfare has published a monograph on antiperspirant products for human use. Most of the active antiperspirants are aluminum halides or complexes thereof. Representative antiperspirants that can be utilized in the dispensing system of the invention are:

Aluminum bromohydrate
Aluminum dichlorohydrate
Aluminum chlorohydrex PG
Aluminum dichlorohydrex PG
Aluminum sesquichlorohydrex PEG
Aluminum chloride
Aluminum zirconium chlorohydrates
Aluminum zirconium trichlorohydrate
Aluminum zirconium trichlorohydrex
Aluminum zirconium pentachlorohydrate
Aluminum zirconium pentachlorohydrex Gly
Aluminum zirconium tetrachlorohydrate
Aluminum zirconium tetrachlorohydrex Gly
Aluminum zirconium octachlorohydrate
Aluminum zirconium octachlorohydrex Gly
Aluminum chlorohydrate
Aluminum sesquichlorohydrate
Aluminum sesquichlorohydrex PG
Aluminum chlorohydrex PEG
Aluminum dichlorohydrex PEG
Aluminum sulfate
Buffered aluminum sulfate
Potassium aluminum sulfate
Sodium aluminum chlorohydroxy lactate The antiperspirant material may be incorporated into the formulation either as a solid or in solution. In the former case, the stearate and the hydrophobic silica are blended together with the solid antiperspirant and this is then fed into a vortex of a mixer containing water and any optional material which may be dissolved or suspended therein. In the latter case, the preformed blend of stearate and hydrophobic silica is fed into the vortex of a mixer containing in the aqueous phase a suspension or solution of the antiperspirant material plus any optional materials to be incorporated in the aqueous phase. If desired, the antiperspirant may be incorporated in the integral aqueous phase or in the external powder phase or in both phases. In another procedure the aqueous and powder phases are separately formulated and are then combined and blended.

The system of the invention will now be illustrated by the following examples which are presented for purposes of illustration only and not intended to limit the invention.

All formulations are for 200 grams. Identification of the materials is provided in the following table:

TABLE 3

| | |
|---|---|
| T 500 | Tullanox 500 (hydrophobic silica) |
| Zn (St)$_2$ | Zinc Stearate |
| Propaloid T | A refined hectorite ore chemically modified to improve hydration properties |
| Vulca 90 | A cross-linked, insoluble, glyceryl starch |
| ACH 50% | 50% Aqueous solution of Aluminum Chlorhydrate |
| Cab-O-Sil | Fumed Silica |
| Rezal 36G | Aluminum Zirconium Chlorhydroxide-35% aqueous solution |
| AlCl$_3$.6H$_2$O | Aluminum Chloride Hexahydrate |
| Finsolv TN | C$_{12}$-C$_{15}$ Alcohols Benzoate |

Examples of the roll-on system follows:

EXAMPLE I

Antiperspirant Roll-on Product

| Material | % W/W |
|---|---|
| 1. Tullanox 500 | 4.25 |
| 2. Zinc Stearate | 1.00 |
| 3. Propaloid T | 2.00 |
| 4. Aluminum Oxide C | 1.00 |
| 5. Vulca 90 | 2.00 |
| 6. Aluminum Chlorhydroxide, 50% Aqueous Solution | 50.00 |
| 7. Aluminum Oxide C | 1.00 |
| 8. Water | 37.50 |
| 9. Dow-Corning 345 Fluid | 0.25 |
| 10. Spray Dried Fragrance | 1.00 |

Processing instructions

A. Combine 1-4 and blend at high speed for ten seconds in a Waring Blender.
B. Combine 5-8 and blend at high speed for thirty seconds in a Waring Blender.
C. Add 9 to B and blend at high speed for five seconds in a Waring Blender.
D. Add A to C and blend at high speed for fifty seconds in a Waring Blender.
E. Add 10 to D and blend at high speed for five seconds in a Waring Blender.

The density of the bulk is 0.63 g/cc.

The product contains 25% active aluminum chlorhydroxide astringent salt. When applied to the axilla using ten strokes, the amount of application was approximately 300 mg which is equivalent to 75 mg of the astringent salt. The aqueous microencapsulation of the astringent salt, which is a powdery substance, was converted to a lotion with excellent adhesion and virtually no powdery fall-out. The application dried in approximately fifteen seconds with little apparant tackiness. A 0.995 inch polyethylene ball and standard polyethylene housing were used in the above test.

EXAMPLE II

Antiperspirant Roll-on Product

| Material | % W/W |
|---|---|
| 1. Tullanox 500 | 4.25 |
| 2. Zinc Stearate | 2.00 |
| 3. Propaloid T | 4.00 |
| 4. Vulca 90 | 4.00 |
| 5. Cab-O-Sil | 1.00 |
| 6. Aluminum Zirconium Chlorhydroxide, 35% Aqueous Solution (Rezal 36G) | 83.50 |
| 7. Spray Dried Fragrance | 1.00 |

Density of bulk=0.56 g/cc

Processing instructions

Same as for Example I.

EXAMPLE III

Antiperspirant Roll-on Product

| Material | % W/W |
|---|---|
| 1. Tullanox 500 | 4.5 |
| 2. Zinc Stearate | 2.0 |
| 3. Propaloid T | 4.0 |
| 4. Aluminum Chloride Hexahydrate | 15.0 |
| 5. Cab-O-Sil | 1.0 |
| 6. Water | 1.0 |
| 7. Spray Dried Fragrance | 1.0 |

Density of bulk=0.53 g/cc

Processing instructions

Same as for Example I.

Many of the air suspension formulations disclosed in the previously referenced patent applications can be dispensed from a roll-on. The suspension is destabilized by the shear forces experienced during pickup by the ball, passing through the annular opening and rubbing during deposition on the skin of the user.

The following compositions were prepared for an efficacy study of the air emulsion suspension roll-on application.

EXAMPLE IV

| Ingredient | % W/W |
|---|---|
| Rezal 36G (35% aqueous solution) | 83.5 |
| Vulca 90 | 4.0 |
| Tullanox 500 | 4.5 |
| Zinc stearate USP | 2.0 |
| Cab-O-Sil | 1.0 |
| Fragrance SL79-868 (Spray Dried) | 1.0 |
| Propaloid T (NL) | 4.0 |
| | 100.00% |

EXAMPLE V

| Ingredient | % W/W |
|---|---|
| Rezal 36G (35% aqueous solution) | 83.5 |
| Tullanox 500 | 4.5 |
| Propaloid T | 4.0 |
| Vulca 90 | 3.6 |
| Zinc stearate USP | 2.0 |
| Spray Dried Fragrance compound PFW Carrier No. 4C (36% oil) | 1.4 |
| Cab-O-Sil M5 | 1.0 |
| | 100.00% |

EXAMPLE VI

| Ingredient | % W/W |
|---|---|
| Rezal 36G (35% aqueous solution) | 83.5 |
| Tullanox 500 | 4.85 |
| Vulca 90 | 3.00 |
| Propaloid T | 2.65 |
| Zinc stearate USP | 2.00 |
| Encapsulated Fragrance Compound (PFW Carrier No. 4C, PFW fragrance oil) | 2.00 |
| Finsolv TN | 1.00 |
| Cab-O-Sil M5 | 1.00 |
| | 100.00% |

EXAMPLE VII

| Ingredient | % W/W |
|---|---|
| Rezal 36G (35% aqueous solution) | 83.5 |
| D.I. Water | 16.5 |
| | 100.00% |

EXAMPLE VIII

| Ingredient | % W/W |
|---|---|
| Rezal 36G (35% aqueous solution) | 85.2 |
| Tullanox 500 | 4.847 |
| Vulca 90 | 3.06 |
| Propaloid T | 2.602 |
| Zinc stearate USP | 2.041 |
| Finsolv TN | 1.23 |
| Cab-O-Sil M5 | 1.02 |
| | 100.000% |

EXAMPLE IX

A nationally marketed roll-on antiperspirant, Dry Idea, consisting of a suspension of an aluminum/zirconium chlorhydrate in a volatile silicone oil modified with suspending agents was included in the following antiperspirant studies.

Four antiperspirant studies were run including two studies which tested compositions of the invention (Examples IV and VIII) against an aqueous solution containing the same antiperspirant in the same concentration as that in the product on the market. Two other compositions of the invention (Examples V and VI) were tested against a product on the market (Example IX) known to have the maximal efficacy exhibited by the aqueous control (Example VII). Therefore, if the first tests showed that the compositions of the invention exhibited efficacy lower than the aqueous control, it would be anticipated that the commercial product of Example IX would also exhibit better efficacy than the compositions of the invention. If the first test showed parity efficacy, the composition position of the invention should also exhibit comparable efficacy to the commercial product (Example IX). Conversely, if the first test showed the compositions of the invention to have better efficacy than the aqueous control, this would be totally unexpected and one would predict that the composition should be more efficacious than the commercial product.

The results were:

Test 1—16 subjects—The aqueous air suspension roll-on of Example IV was applied to one axilla and the aqueous solution of Example VII was applied to the other axilla of each subject (about 0.25 gms). The powder roll-on was 12.55% more effective than the aqueous solution. Hypothesis test of the difference between the means of the two treatments showed a probability of 0.07.

Test 2—36 subjects—The aqueous air suspension of Example V was tested versus no treatment and versus the commercial product and the commercial product was tested versus no treatment. Example V was found to have 64.5% efficacy vs. 59.1% for the commercial product. Hypothesis test of the mean differences gave probability of less than 0.10%.

Test 3—16 subjects—Example VII applied to one axilla, and Example VIII was applied to the other. The powder roll-on was 19.0% more effective than the aqueous solution. Hypothesis tests of the differences between the means of the two treatments gave probability of 0.08.

Test 4—36 subjects—The air emulsion of Example VI was tested versus the commercial product and versus no treatment. The commercial product was also tested versus no treatment. Example VI was found to have 63.3% efficacy vs. 59.4% for the commercial product. Hypothesis tests of the mean differences between the two products gave probability greater than 0.10.

On the average, testing the product of the invention versus a solution of its active ingredient showed the product to be about 15% more efficacious. This is a surprising result indicating that the vehicle has enhanced the efficacy of the active ingredient. One possible rationale is that the Tullanox may prevent the active from being washed away by perspiration because of its hydrophobic nature, thus making more of the active available to perform its antiperspirant function. The other two tests confirm that the product should be more active than competitive products.

An investigation of the system produced the following observations:

1. The product after shearing action by the roll-on dries more quickly and is less sticky than a conventional aqueous based roll-on.
2. The concentration of water in the product is approximately equal to that of a conventional roll-on.
3. The antiperspirant activity as measured is at least equivalent to an aqueous solution of the active.

These observations are not to be expected. The effect of shearing is to change the system from a free-flowing powder to a cream or lotion with the aqueous phase no longer encapsulated. If that is true, then it is difficult to explain why the product quickly dries and is non-sticky. The original free-flowing powder like material is dry to the touch and this has been recognized in the past. It has never been recognized that the product after shear should retain this dry feel. If the reason is that the active in water has not been completely released, then it would be expected that there would not be antiperspirant activity equivalent to the aqueous solution. This is contrary to the results of the antiperspirant efficacy experiment. One possible explanation may be that even though the effect of shearing is to release the aqueous solution of the active completely, the inherent dryness of the hydrophobic metal oxide is sufficient to give a perception of dryness and lack of stickiness to the user. This would then permit the active to work maximally without the associated negatives of wetness and stickiness.

Efficacy studies show that maximum efficacy is achieved by roll-on application when compared to an aqueous solution of the active ingredient. Moreover, the more effective aluminum-zirconium salts are permitted in roll-on formulations but are prohibited in spray applications.

The stickiness, tackiness, oiliness and lengthy dry-out time of conventional lotion roll-on application is overcome by means of a free-flowing aqueous microencapsulation of the antiperspirant chemical which displays good flowability through the annular space between the ball and socket without sacrificing the efficacy associated with conventional roll-on forms of product. This invention achieves good application aesthetics and flow characteristics with good adhesion of the product and without undesirable powder fall-out.

The basis of this invention is an aqueous microencapsulation, said aqueous phase being reduced to small droplets by high intensity mixing and stabilized with a hydrophobic metal oxide. Bioactive materials such as astringents or antimicrobial agents, or other materials such as fragrances or pigments used for make-up products can be introduced in either the aqueous or hydrophobic metal oxide phase or in both phases. The shear sensitivity of the bulk is adjusted so that during its passage through the roll-ball applicator and application to the substrate, the microencapsulated powdery substance is converted to a lotion with good adhesion. The more shear resistant the bulk, the drier the lotion. The final shear sensitivity is a function of the intensity of mixing, the nature and amount of hydrophobic metal oxide, the nature and amount of system affecting additives, the nature and amount of the bioactive substances or other substances such as fragrance, and other factors. The net shear effect, however, is the sum of the shear effects of the product as it passes through the annular space comprising the ball and housing dispenser and applicator, and the subsequent shear effect of the ball applicator applying the product to the substrate.

Thus, the invention demonstrates the use of shear to provide products of varying properties from powdery particles to creamy applications. During processing of the bulk sufficient energy is added by high speed mixing to render the bulk shear sensitive so that on passage through an outlet of preselected clearance a controlled amount of destabilization and coalescence can occur. The clearance is sized to impart an amount of shear effective to at least partially destabilize the interfacial barrier. At the point of total coalescence the barrier is destroyed and the internal, discontinuous water phase becomes an external continuous phase. At coalescence, the hydrophobic metal oxide appears to impart water resistance to the surface of the target such as the skin of the user. The delivery rate can be varied over wide ranges from 40 to 500 mg per application usually 60 to 300 mg per application.

Three hundred samples of the water-in-air suspension antiperspirant composition of Example VI were packaged in a plastic molded bottle containing an integrally molded fitment receiving a 1.000 inch ball. The samples were tested for delivery rate, in milligrams for each sample per axilla, fall-out, dusting and density. In each case seven passes or strokes were used to apply the product to the axilla in amounts from 190 to 360 milligrams per application. There was no perception of oiliness or tackiness after application.

With respect to fall-out of unsheared powder on a rating scale of from 0 (no fall-out) to 4 (maximum fall-out) only a portion of the samples in the 300 milligram application range exhibited some fall-out (rating of 1). No sample received rating higher than 1.

Dusting was evaluated by a visual observation of powder which became airborne during application. Using a similar rating, dusting was only observed for some of the large application samples and no sample received a rating higher than 1.

Initial and twenty-four hour densities are recorded below for a number of the batches:

DENSITY DETERMINATIONS

| Mixing time seconds | Production Density, d | 24 hour Density, d | Mixing time seconds | Production Density, d | 24 hour Density, d |
|---|---|---|---|---|---|
| 90 | .68 | — | 85 | .67 | .66 |
| 100 | .69 | — | 90 | .67 | .66 |
| 80 | .68 | — | 105 | .68 | .66 |
| 115 | .68 | — | 90 | .67 | .66 |
| 90 | .69 | — | 75 | .67 | .65 |
| 75 | .67 | — | 85 | .68 | .65 |
| 85 | .68 | — | 90 | .68 | .65 |
| 95 | .68 | — | 85 | .68 | .66 |
| 75 | .67 | — | 100 | .68 | .66 |
| 75 | .67 | — | 80 | .68 | .66 |
| 75 | .67 | .66 | 95 | .68 | .67 |
| 85 | .68 | .67 | 100 | .69 | .67 |
| 80 | .67 | .65 | 75 | .69 | .67 |
| 95 | .69 | .67 | 95 | .69 | .67 |
| 90 | .67 | .66 | 75 | .68 | .67 |
| 80 | .68 | .67 | 85 | .68 | .68 |
| 100 | .68 | .68 | 90 | .69 | .68 |
| 95 | .68 | .65 | 110 | .68 | .68 |
| 80 | .67 | .65 | 80 | .68 | .66 |
| 85 | .69 | .68 | 85 | .68 | .67 |
| 70 | .67 | .65 | 80 | .69 | .68 |
| 80 | .67 | .66 | 80 | .68 | .66 |

It is to be realized that only preferred embodiments of the invention have been described and that numerous substitutions, modifications and alterations are permissible without departing from the spirit and scope of the invention as defined in the following claims.

We claim:

1. A roll-on deodorant or antiperspirant powdery cream or lotion composition comprising a roll-on system for applying said composition to the axillae of a user comprising in combination:
a container including;
a compartment within the container receiving;
said composition which comprises a stabilized water-in-air suspension including a discontinuous liquid phase comprising small, discrete, stable droplets of aqueous liquid, each droplet of said liquid being coated and stabilized with an interfacial barrier of very fine, hydrophobic metal oxide particles of the formula $_eO\text{-}MR_aX_b$ where e represents the oxide surface; O is oxygen; M is metal selected from the group consisting of silicon, titanium, aluminum, zirconium, vanadium, iron or mixtures thereof, R is an organo group selected from the group consisting of alkyl, aryl, arylalkyl, alkoxy and aryloxy, a is a number from 1 through 3, X is a halogen or hydroxy b is a number from 0 through 2, $a+b=3$ and containing at least 0.5% by weight of said organo groups, said coated droplets being suspended in an external air phase such that the density is from 0.3 to 1.5 g/cc and the ratio of hydrophobic metal oxide to aqueous liquid being from 1/1 to 50/1 and the suspension including in parts by weight:
25% to 98.9% of aqueous liquid;
1% to 15% hydrophobic metal oxide, and
0.1% to 16% deodorant or antiperspirant compound;
a seat member; and
a rotating member received by solid seat member to define an outlet therebetween through which said suspension is dispersed onto said axillae from said compartment on rotation of said member;
said outlet being sized to apply preselected shear to said suspension in an amount sufficient to at least partially destabilize the suspension to coalesce at least 10% of said droplets into larger droplets.

2. A roll-on deodorant or antiperspirant powdery cream or lotion composition comprising a roll-on system according to claim 1 wherein the rotating member is a rotating ball and the outlet is an annular opening between the rotating ball and the seat member.

3. A roll-on deodorant or antiperspirant powdery cream or lotion composition comprising a roll-on system according to claim 2 in which sufficient shear is applied to said droplets during passage through said annular opening to form a continuous phase cream or lotion.

4. A roll-on deodorant or antiperspirant powdery cream or lotion composition comprising a roll-on system according to claim 1 in which the composition includes an antiperspirant salt.

5. A roll-on deodorant or antiperspirant powdery cream or lotion composition comprising a roll-on system according to claim 4 in which the density of the suspension is from 0.3 to 1.5 g/cc and the ratio of hydrophobic metal oxide to aqueous liquid is from 1/1 to 50/1.

6. A roll-on deodorant or antiperspirant powdery cream or lotion composition comprising a roll-on system according to claim 1 in which the hydrophobic oxide is a silane treated silica.

7. A roll-on deodorant or antiperspirant powdery cream or lotion composition comprising a roll-on system according to claim 6 in which the hydrophobic metal oxide is a pyrogenic silica.

8. A roll-on deodorant or antiperspirant powdery cream or lotion composition comprising a roll-on system according to claim 1 in which an antiperspirant compound is present in an amount from 5% to 45% by weight, the hydrophobic metal oxide is present in an amount from 3 to 10% by weight, water is present in an amount from 30 to 80% by weight and further including from 0 to 5% of a shear control agent.

9. A roll-on deodorant or antiperspirant powdery cream or lotion composition comprising a roll-on system according to claim 8 in which the antiperspirant compound is an aluminum-halogen compound having at least one Al-halo bond.

10. A roll-on deodorant or antiperspirant powdery cream or lotion composition comprising a roll-on system according to claim 9 in which the antiperspirant compound is an aluminum-zirconium compound.

* * * * *